United States Patent
Heller et al.

Patent Number: 5,954,728
Date of Patent: Sep. 21, 1999

[54] FILLING APPARATUS FOR BONE CEMENT

[75] Inventors: Mathias Heller, Winterthur, Switzerland; Hans-Georg Willert, Göttingen, Germany

[73] Assignee: Sulzer Orthopaedie AG, Baar, Switzerland

[21] Appl. No.: 09/050,602

[22] Filed: Mar. 30, 1998

[30] Foreign Application Priority Data

Apr. 16, 1997 [EP] European Pat. Off. ............ 97810235

[51] Int. Cl.⁶ .................................................. A61B 17/56
[52] U.S. Cl. ............................... 606/92; 606/86; 606/93
[58] Field of Search .................. 606/92, 93, 94, 606/86

[56] References Cited

U.S. PATENT DOCUMENTS

| | | |
|---|---|---|
| 2,836,333 | 5/1958 | Woodel . |
| 4,466,435 | 8/1984 | Murray ....................................... 606/94 |
| 4,625,722 | 12/1986 | Murray ....................................... 606/94 |
| 4,627,434 | 12/1986 | Murray ....................................... 606/94 |
| 5,322,381 | 6/1994 | Argo, II . |
| 5,468,245 | 11/1995 | Vargas, III . |
| 5,501,687 | 3/1996 | Willer et al. ............................... 606/94 |

FOREIGN PATENT DOCUMENTS

0628295A1 12/1994 European Pat. Off. .
2105198 3/1983 United Kingdom .

Primary Examiner—Michael Buiz
Assistant Examiner—Daphna Shai
Attorney, Agent, or Firm—Townsend and Townsend and Crew LLP

[57] ABSTRACT

The invention shows a filling apparatus for the introduction of bone cement into the intramedullary cavity of a bone, preferably into the cavity of a femur bone. The apparatus has a filling cannula, at the end of which a rubber sleeve in the form of a sheet metal bell is fastened which projects with its movable part radially beyond the diameter of the filling cannula and axially beyond a lowermost outlet aperture of the filling cannula. Because the sleeve is executed in the lower expandable part with a thickness 1 mm<s<2 mm and is fastened above an uppermost outlet aperture of the filling cannula at a distance 3 mm<l<50 mm and projects with its lower edge beyond a lowermost deflection edge 11a of a lower outlet aperture by a distance 5 mm<a<50 mm, its cross-section adapts to the cavity wall when being introduced without getting caught up and seals it during the expulsion of the bone cement.

15 Claims, 4 Drawing Sheets

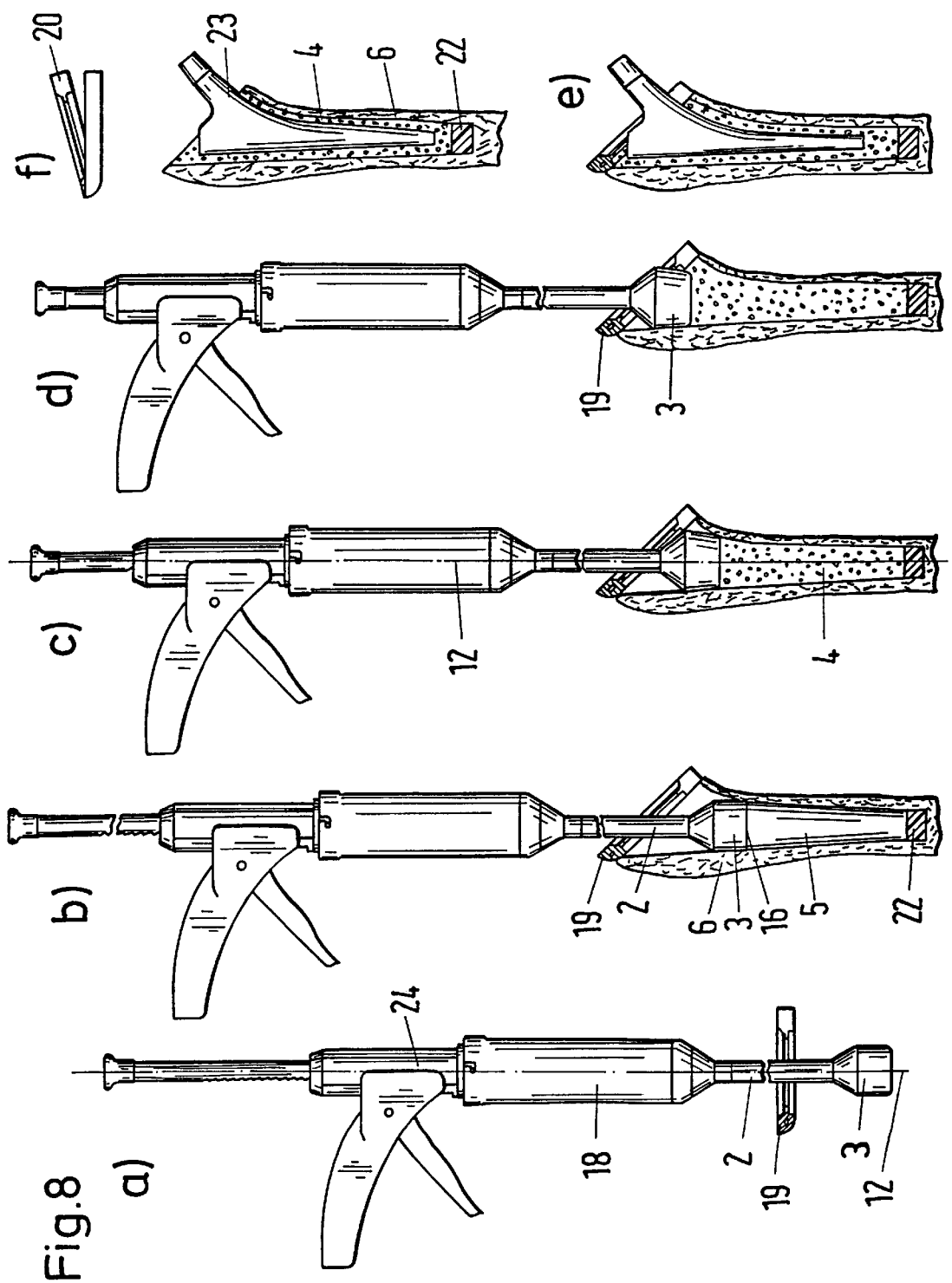

FILLING APPARATUS FOR BONE CEMENT

BACKGROUND OF THE INVENTION

The invention relates to a filling apparatus for the introduction of bone cement into the intramedullary cavity of a bone, preferably into the cavity of a femur bone, with a filling cannula, at the end of which a hose-like sleeve is fastened which can be radially expanded under the pressure of emerging bone cement.

Filling apparatuses are described in EP-A-0 628 295. Flexible extensions of a filling cannula are shown there as sleeves, which have a material reserve at their free end which is formed by overlapping elasticity or folding. Filling apparatuses of this kind have the disadvantage that, when the filling cannula is being moved into the intramedullary cavity, they encounter the cavity wall with the jacket edge before the actual end of the cavity is reached. In the event that the sleeve is too stiff, there is the problem that its elasticity is not sufficient to produce a sufficient sealing pressure at a widening cavity cross-section during the filling of the intramedullary cavity. It is also not of much use if the diameter of the filling cannula and the sleeve is chosen to be particularly small, since new problems arise thereby. On the one hand, the expulsion is made more difficult due to the continuously increasing viscosity of the bone cement, and on the other hand, even higher requirements are placed on the sleeve with respect to stretching.

Other embodiments, such as GB-A-2 105 198, presuppose additional elements such as axially displaceable protective sleeves on a filling cannula the end of which is formed as an erectible umbrella with ribs and films lying between them.

SUMMARY OF THE INVENTION

The object of the invention is to provide a simple filling apparatus which enables an intramedullary cavity to be filled from one end with bone cement against a manually produced counter-pressure.

This object is satisfied in that in a longitudinal section the movable part of the sleeve has the form of a sheet metal bell projecting radially beyond the diameter of the filling cannula and axially beyond a lowermost outlet aperture of the filling cannula.

A filling cannula of this kind has the advantage that it can be placed in the cavity base without delay, i.e. without placing demands on a strongly fluctuating portion of the hardening time of the bone cement. A further advantage is that when it is moved into oval cavity cross-sections, a position is automatically assumed which counteracts too great a local over-stretching of the sleeve when being moved out under pressure. The filling cannula can be lowered down to the cavity base at a medullary space barrier and produces a large and noticeable counter-force when it makes contact. When being lowered into the cavity base, the rather oval cross-section deforms without problem into a round cross-section through the side pressure of the cavity wall. Nevertheless, a cross-section which is actually oval is available in the proximal region for the deformation under pressure.

Inflation and contact of the sleeve results when the lower edge of the sleeve projects by a distance 5 mm<a<50 mm beyond a lowermost lateral deflection edge of the lowermost outlet aperture, when the expandable part of the sleeve is fastened at a distance 3 mm<l<50 mm above an uppermost lateral outlet edge of the filling cannula, and when the expandable part of the sleeve consists of rubber with a thickness 1 mm<s<2 mm.

Through the dimensions selected, a sleeve arises which seals so well that the surgeon himself determines the pressure at which the filling cannula and the sleeve ride upwardly on the bone cement by the weight he places on the filling apparatus.

A filling cannula with lateral outflow apertures has the advantage that the outflow aperture is fully open even at the beginning, and thus uniform conditions can be provided for the expulsion of bone cement independently of the surgeon. In addition the apparatus can be lowered toward the cavity base only up to that point at which the base of the filling cannula hits bottom. With a Shore hardness of Shore A35, a thickness S of 1.5 mm has proved satisfactory for the expandable part of the sleeve, with a sleeve having optimal resistance for femur bones when being moved in and out under pressure resulting from the distances a=15 mm and l=20 mm for frontal outlet apertures and the distances a=15 mm and l=5 mm for lateral outlet apertures. In a filling cannula with a round cross-section a sleeve which is round in its clamping cross-section is fastened to the filling cannula, for example with a clamping clip, with the cross-section expanding to form a bell with an elliptical cross-section. In this region of growing cross-section the wall thickness s can be enlarged to over 2 mm in order to prevent the sleeve from turning over under internal pressure. The safety against the sleeve's becoming caught during the lowering can be additionally increased by a drawing in of the lower edge.

The filling cannula can be connected to an expulsion cylinder, from which the mixed bone cement is pressed out with an expulsion piston.

Prior to moving the sleeve in, it is advantageous to push on a seal onto the filling cannula between the sleeve and the expulsion cylinder in order to have a closure seal in the proximal cavity for the later expulsion of bone cement and to possess an aid to orientation for an artificial femur shaft to be lowered later. For this reason the seal is made transparent, which facilitates its positioning on a resected femur bone, and is equipped with elastic lips of rubber on its inner side, which enable a pulling out of the filling cannula with the sleeve.

After the lowering of the artificial femur shaft, the seal remains in place until the bone cement has hardened. The bone cement which wells out when the prosthesis is lowered is removed beforehand. After the hardening has taken place the seal can be removed, by its either being cut open or being designed from the beginning as a removable slit ring. In the latter case a reinforcement clip matched to the shape is advantageous.

BRIEF DESCRIPTION OF THE DRAWINGS

FIGS. 8*a*, *b*, *c*, *d*, *e*, *f* are schematic views illustrating procedure for the filling with bone cement and the insertion of the prosthesis shaft;

DESCRIPTION OF THE PREFERRED EMBODIMENTS

Figure 2:
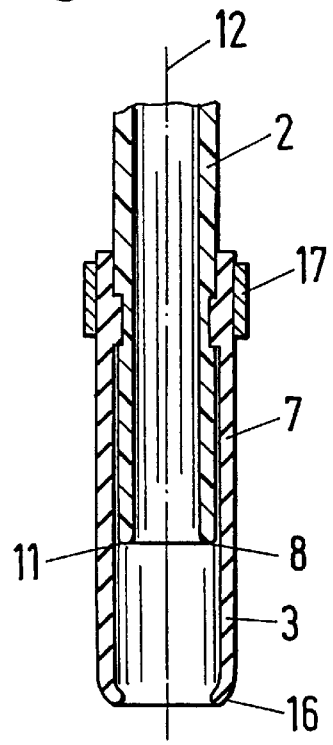
FIG. 2 is a schematic longitudinal section through the sleeve of FIG. 1 displaced by 90°.

The figures show a filling apparatus for the introduction of bone cement into the intramedullary cavity of a bone, preferably into the cavity of a femur bone. The apparatus has a filling cannula 2, at the end of which a rubber sleeve 3 in the form of a sheet metal bell 9 is attached which has a movable part 7 which projects radially beyond the diameter of the filling cannula 2 and axially beyond a lowermost outlet aperture of the filling cannula 2. Since the sleeve 3 is designed to have a thickness 1 mm<s<2 mm in the expandable lower part and is fastened above an uppermost outlet aperture 13 of the filling cannula at a distance 3 mm<1<50 mm and projects downwardly beyond a lowermost lateral deflection edge 11*a* of a lowermost outlet aperture by a distance 5 mm<a<50 with its lower edge 16, it matches its cross-sectional form to the cavity wall without becoming stuck and seals it during the expulsion of bone cement.

Figure 1:
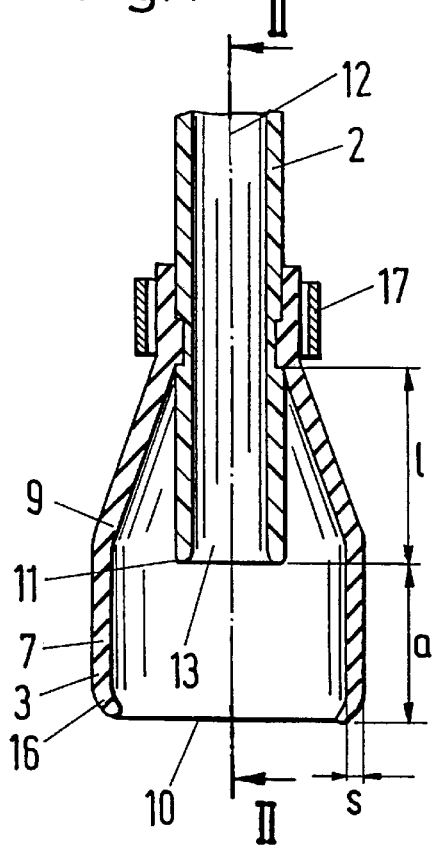
FIG. 1 is a schematic longitudinal section through a filling cannula with a sleeve in accordance with the invention.
Figure 3:
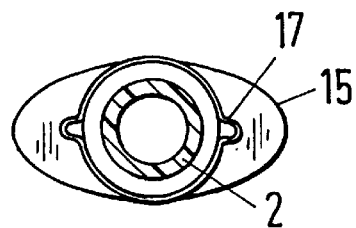
FIG. 3 is a schematic plan view of the filling cannula and the sleeve of FIG. 1.

In FIGS. 1 to 3 the movable part 7 of the sleeve 3 is fastened at a distance 3 mm<1<50 mm above the lateral deflection edge 11 of the uppermost outlet aperture 13 with a clamping clip 17. The movable part 7 consists of rubber, has an elliptical cross-section 15, a wall thickness 1 mm<s<2 mm, and the form of a sheet metal bell 9. At its lower edge 16 the sleeve 3 is drawn inwards and projects beyond the lowermost lateral deflection edge 11*a* of the outlet aperture 13 by a distance of 5 mm<a<50 mm. The outlet aperture 13 is transverse to the axis 12 of the filling cannula at its upper end.

Figure 4:
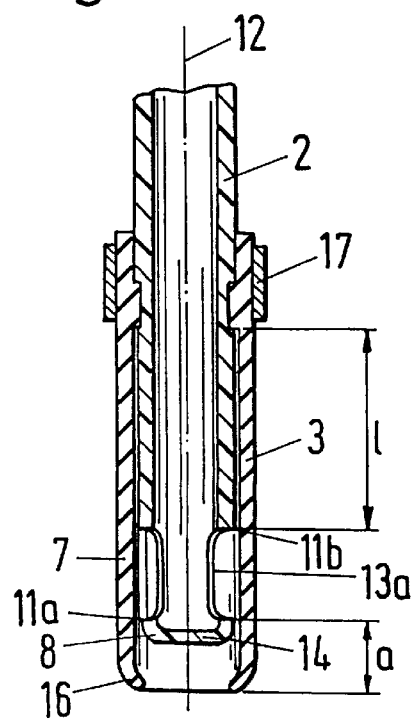
FIG. 4 is a schematic longitudinal section as in FIG. 2, however with a filling cannula with lateral outlet apertures.

FIG. 4 shows a further example of a filling cannula 2 with lateral outlet apertures 13*a* and a base 14 at its end 8. The sleeve 3 corresponds to that of FIGS. 1 to 3 and diverges likewise from its clamping location 17 to a movable part 7 having the form of a sheet metal bell 9 with an elliptical cross-section. Through the cannula 16 projecting beyond the base 14 and beyond the lowermost lateral deflection edge 11*a* of the outlet apertures 13*a*, a spreading apart and sealing of the sleeve 3 against the cavity wall in order to build up a suitable counter-pressure for the emerging bone cement in the direction of the axis 12 of the filling cannula is ensured even in the event that the filling cannula 2 is not placed gently in contact with the cavity base. The clamping location 17 is spaced at a distance 1 from an uppermost lateral deflection edge 11*b* of the outlet bores 13*a*.

Figure 5:
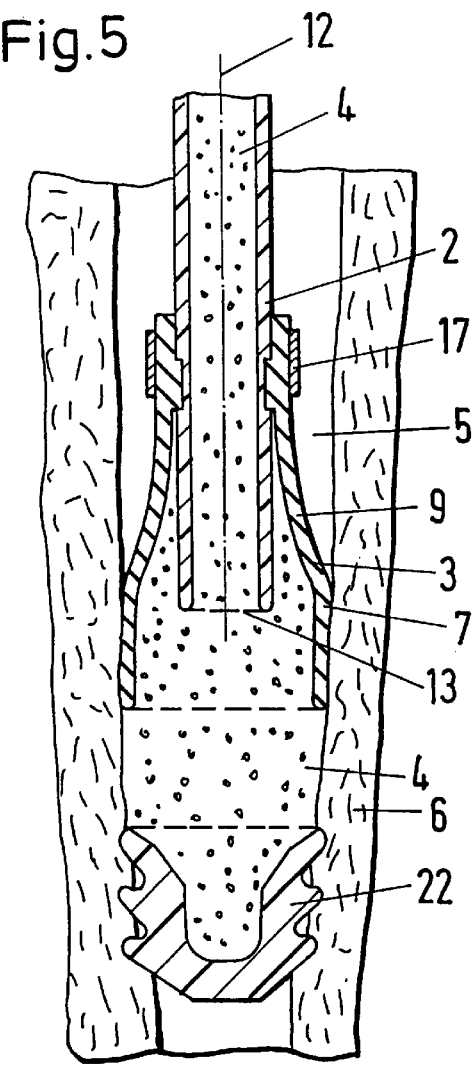
FIG. 5 is a schematic partial section of a tubular bone with a medullary space barrier and a filling cannula with a sleeve in accordance with FIG. 1 in the process of rising.

In FIG. 5 a femur bone 6 is closed off by a medullary cavity barrier 22. Bone cement 4 is expelled from the outlet aperture 13 and has already filled the space between the sleeve 3 and the medullary cavity barrier 22. An air cushion was still present when the expandable part 7 of the sleeve encountered the medullary cavity barrier 22. This has been displaced by the emerging bone cement and has departed upwardly between the cavity wall 5 and the sleeve 3. It is conceivable to arrange a small venting aperture at a small distance ahead of the clamping location 17 in the movable part 7 of the sleeve or above the clamping location, through which the air can just barely escape. The filling cannula is then held at its lowermost position until the air present is displaced. The bone cement which follows expands the sleeve against the cavity wall 5 and at the same time thrusts it upwards in accordance with the amount of bone cement expelled. The surgeon feels the lifting movement and can manually exert a corresponding counter-pressure in order to force the bone cement into recesses of the cavity wall 5 while it is being deposited.

Figure 10:
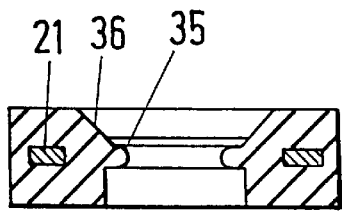
FIG. 10 is a schematic section through the seal of FIG. 6.
Figure 6:
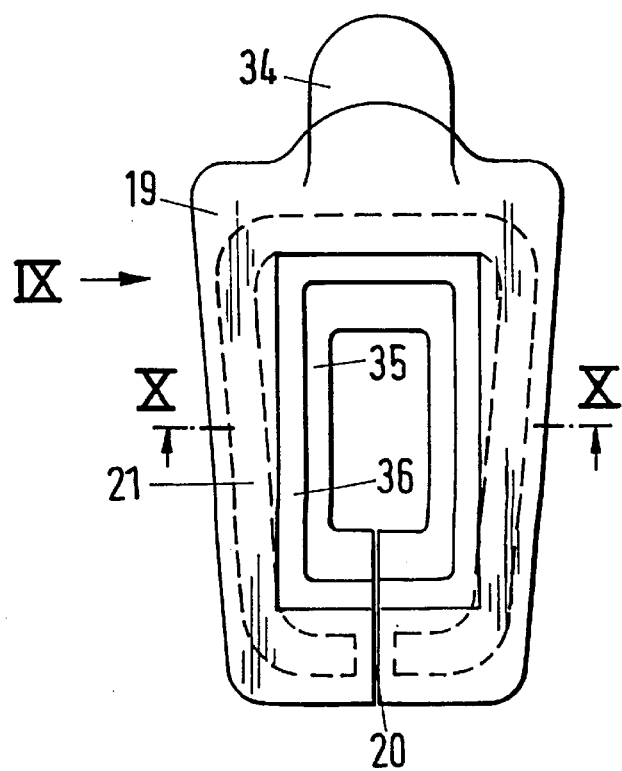
FIG. 6 is a schematic plan view of a seal which is executed as a slit ring with a wire clamp.
Figure 9:
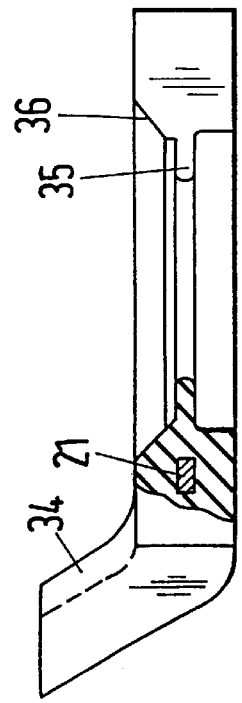
FIG. 9 is a schematic view with a partial section through the seal of FIG. 6.

FIGS. 6, 9 and 10 show a seal 19 of silicone rubber which can be pushed onto the filling cannula 2 in order to achieve a sealing effect in the proximal region of a femur bone 6 and to be able to press out the bone cement up to the end of the resected bone under pressure. The seal 19 is executed as a slit ring 20 in which a wire hoop 21 is inserted for stiffening. The central aperture is bounded by an elastic lip 35 through which the sleeve 3 can be pulled out under lateral pressure. The dimensions of the lip and of the sleeve are matched to the proximal part of a prosthesis shaft later to be inserted in such a manner that the lip also provides a guidance for the proximal part of the prosthesis at the same time. There is an entry to the lip 36 in the form of a bevel 35 which assists in the centering of the prosthesis shaft and on which the superfluous bone cement collects during the introduction of the prosthesis shaft to be wiped off. The elastic part of the seal 19 consists of transparent material in order to be able to check on the position of the seal 19 when it is being positioned on the resected surface. A lateral holding grip 34, which comes to lie in the extension of the great trochanter, is formed on the seal 19.

Figure 7:
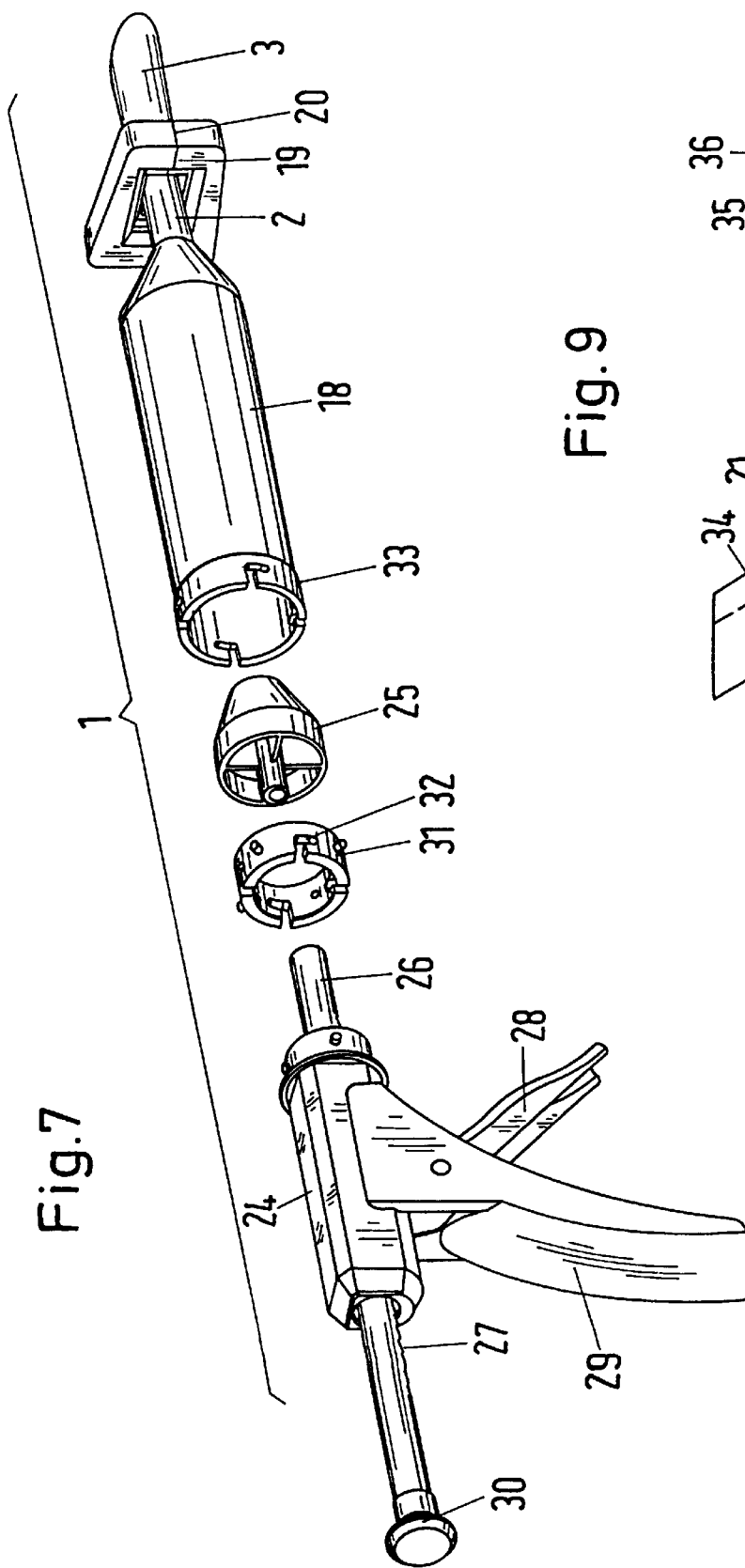
FIG. 7 is a schematic exploded view of a filling apparatus for bone cement.

In FIG. 7 the main components of a filling apparatus 1 are displayed. The filling cannula 2 is connected to an ejection cylinder 18. A seal 19 in the form of a slit ring 20 is pushed on between the sleeve 3 and the ejection cylinder 18. Bone cement (not shown here) is brought into the expulsion cylinder 18 in mixed form or is mixed in the expulsion cylinder. A piston 25 closes off the ejection cylinder. A coupling 31 secures the piston 25 with a bayonet joint 33. A feed device 24 is flanged on via a further bayonet joint 32. A thrust rod 26 which is brought into its rearward position by a retraction button 30 is provided with a rack 27 which enables a step-wise forward thrust movement via a lever 28 and a non-illustrated pawl. The entire filling apparatus can be held by a pistol grip 29 and the forwarding can be actuated with one hand.

The principles of the use of the filling apparatus 1 are illustrated in the FIGS. 8*a* to *f*. FIG. 8*a* shows an assembled filling apparatus filled with bone cement, comprising a sleeve 3, a filling cannula 2, a seal 19, an ejection cylinder 18, and a forward thrust device 24. In FIG. 8*b* the seal 19 has already been placed on a prepared femur bone 6 and the filling cannula 2 and the sleeve 3 move into a prepared intramedullary cavity 5 until the lower edge 16 of the sleeve arrives at a medullary cavity barrier 22, the depth of which had previously been measured and can be compared with a scale for the immersion depth on the filling cannula. Through actuation of the feed device a situation arises such as has been described in detail in connection with FIG. 5. The filling apparatus in FIG. 8*c* is pushed upwards in accordance with the expelled volume of bone cement 4. The surgeon determines how great the pressure on the bone cement is when it is being deposited in the intramedullary cavity with his counter-force in the direction of the axis 12. In FIG. 8*d* the sleeve 3 is already half clamped in the seal 19. This is the moment at which the filling apparatus is pivoted to the right about an imaginary center of rotation at the seal 19 in order to completely fill the space under the seal with bone cement and to pull the sleeve 3 out completely. Guided by the seal 19, a femur prosthesis shaft is now introduced until its end position has been reached, as illustrated in FIG. 8*e*, with a pressure being maintained on the bone cement in the intramedullary cavity by the seal. The excess bone cement pressed out at the seal is wiped off. After the bone cement has hardened, the seal can be spread open as a slit ring as in FIG. 8f and removed from the prosthesis shaft 23. A cement jacket 4 without cavities has now arisen between the prosthesis shaft 23 and the femur bone 6.

We claim:

1. A filling apparatus for the introduction of bone cement into the intramedullary cavity of a bone, the filling apparatus comprising a filling cannula having a hose-like sleeve fastened at an end thereof, the sleeve having a longitudinal section with an expandable part which is radially expandable under pressure of emerging bone cement, wherein the filling cannula has a lowermost outlet aperture which is closed off by a base and has lateral outlet apertures above the base, and wherein the expandable part of the sleeve has a sheet metal bell form which projects radially beyond the diameter of the filling cannula and axially to a lower edge beyond the lowermost outlet aperture of the filling cannula.

2. A filling apparatus in accordance with claim 1 wherein the lower edge of the sleeve projects by a distance greater than 5 mm and less than 50 mm beyond a lowermost lateral deflection edge of the lowermost outlet aperture of the filling cannula, wherein the expandable part of the sleeve is fastened to the filling cannula at a distance greater than 3 mm and less than 50 mm above an uppermost lateral deflection edge of the lateral outlet apertures of the filling cannula, and wherein the expandable part of the sleeve includes rubber and has a thickness greater than 1 mm and less than 2 mm.

3. A filling apparatus in accordance with claim 2 wherein the lower edge of the sleeve projects by a distance of 15 mm beyond the lowermost lateral deflection edge of the lowermost outlet aperture of the filling cannula, and the expandable part of the sleeve is fastened at a distance of 5 mm above the uppermost lateral deflection edge of the lateral outlet apertures of the filling cannula.

4. A filling apparatus in accordance with claim 1 wherein the thickness of the expandable part is 1.5 mm and the sleeve has a Shore hardness of 35A.

5. A filling apparatus in accordance with claim 1 wherein the expandable part of the sleeve is elliptically deformed in cross-section with increasing distance from a location where the sleeve is fastened to the filling cannula.

6. A filling apparatus in accordance with claim 1 wherein the lower edge of the expandable part of the sleeve is drawn inwards to prevent the sleeve from being caught while being lowered into the intramedullary cavity.

7. A filling apparatus in accordance with claim 1 further comprising an expulsion cylinder connected with the filling cannula.

8. A filling apparatus in accordance with claim 7 further comprising a seal pushed on between the expulsion cylinder and the sleeve through which the filling cannula with the sleeve can be withdrawn backwardly with pressure on the sides thereof.

9. A filing apparatus in accordance with claim 8 wherein the seal includes a slit ring of rubber which is reinforced by a wire hoop.

10. A filling apparatus in accordance with claim 8 wherein the seal is transparent to enable the position of the seal to be observed when positioned on a resected bone surface.

11. A filling apparatus in accordance with claim 1 further comprising a clamping clip fastening the sleeve to the filling cannula.

12. A filling apparatus for the introduction of bone cement into the intramedullary cavity of a bone, the filling apparatus comprising:

a filling cannula having an end with a lowermost outlet aperture;

a hose-like sleeve fastened at the end of the filling cannula, the sleeve having an expandable part which is radially expandable under pressure of emerging bone cement, the expandable part of the sleeve having a sheet metal bell form which projects radially beyond the diameter of the filling cannula and axially to a lower edge beyond the lowermost outlet aperture of the filling cannula; and a clamping clip fastening the sleeve to the filling cannula.

13. A filling apparatus for the introduction of bone cement into the intramedullary cavity of a bone, the filling apparatus comprising:

a filling cannula having an end with a lowermost outlet aperture;

a hose-like sleeve fastened at the end of the filling cannula, the sleeve having an expandable part which is radially expandable under pressure of emerging bone cement, the expandable part of the sleeve having a sheet metal bell form which projects radially beyond the diameter of the filling cannula and axially to a lower edge beyond the lowermost outlet aperture of the filling cannula;

an expulsion cylinder connected with the filling cannula; and a seal pushed on between the expulsion cylinder and the sleeve through which the filling cannula with the sleeve can be withdrawn backwardly with pressure on the sides thereof.

14. A filling apparatus in accordance with claim 13 wherein the seal includes a slit ring of rubber which is reinforced by a wire hoop.

15. A filling apparatus in accordance with claim 14 wherein the seal is transparent.

* * * * *